United States Patent
Yori et al.

(10) Patent No.: US 10,806,139 B2
(45) Date of Patent: Oct. 20, 2020

(54) METHOD AND SYSTEM FOR RECOVERY OF LIVING CELLS FROM CRYOPRESERVED CELLS

(71) Applicant: TERUMO KABUSHIKI KAISHA, Shibuya-ku, Tokyo (JP)

(72) Inventors: Kouichirou Yori, Kanagawa (JP); Ryohei Takeuchi, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days.

(21) Appl. No.: 15/274,678

(22) Filed: Sep. 23, 2016

(65) Prior Publication Data

US 2017/0006857 A1    Jan. 12, 2017

Related U.S. Application Data

(63) Continuation of application No. PCT/JP2015/057473, filed on Mar. 13, 2015.

(30) Foreign Application Priority Data

Mar. 25, 2014 (JP) ................................. 2014-062311

(51) Int. Cl.
*A01N 1/02* (2006.01)
*C12N 5/077* (2010.01)

(52) U.S. Cl.
CPC ........... *A01N 1/021* (2013.01); *A01N 1/0247* (2013.01); *C12N 5/0658* (2013.01)

(58) Field of Classification Search
None
See application file for complete search history.

(56) References Cited

U.S. PATENT DOCUMENTS

| 5,789,147 | A | * | 8/1998 | Rubinstein | ............... | A01N 1/02 424/93.7 |
|---|---|---|---|---|---|---|
| 2002/0043503 | A1 | | 4/2002 | Pages | | |
| 2013/0177967 | A1 | | 7/2013 | Kazumura et al. | | |

FOREIGN PATENT DOCUMENTS

| EP | 0 394 788 A1 | 10/1990 |
|---|---|---|
| EP | 2 615 178 A1 | 7/2013 |
| JP | 2007-528755 A1 | 10/2007 |
| JP | 2010-081829 A | 4/2010 |
| JP | 2010-081829 A1 | 4/2010 |
| JP | 2010-226991 A1 | 10/2010 |
| JP | 2011-115058 A | 6/2011 |
| WO | 9838940 A1 | 9/1998 |
| WO | 0033653 A1 | 6/2000 |
| WO | WO 2005-011524 | 2/2005 |
| WO | WO 2012/032853 A1 | 3/2012 |

OTHER PUBLICATIONS

Freshney, R. I. "Cryopreservation." Culture of Animal Cells: A Manual of Basic Technique. 4th ed. New York: Wiley-Liss, 2000. 297-307 Print. (Year: 2000).*
Yokoyama et al, "Cryopreservation and Thawing of Cells" in Current Protocols in Immunology, 2012. Supplement 99: A.3G.1-A.3G.5. (Year: 2012).*
The extended European Search Report dated Jul. 26, 2017, by the European Patent Office in corresponding European Patent Application No. 15770397.6 (6 pgs).
International Search Report (PCT/ISA/210) dated Jun. 16, 2015, by the Japanese Patent Office as the International Searching Authority for International Application No. PCT/JP2015/057473.
Written Opinion (PCT/ISA/237) dated Jun. 16, 2015, by the Japanese Patent Office as the International Searching Authority for International Application No. PCT/JP2015/057473.
Office Action dated Jun. 7, 2018 in corresponding European Patent Application No. 15 770 397.6.
Goto et al., "Studies on Cryopreservation of Fowl Semen for Practical Use (vol. II)—An Examination on Cryopreservation Method of Fowl Semen and Fertilization Test—" Gunma Journal of Agricultural Research, C Animal Husbandry No. 7 (1990), pp. 117-122. (with English translation (32 pages).

* cited by examiner

*Primary Examiner* — Allison M Fox
(74) *Attorney, Agent, or Firm* — Buchanan Ingersoll & Rooney PC

(57) ABSTRACT

A method is disclosed for recovering living cells highly efficiently from cryopreserved cells by thawing and a system designed for such a method. The method for recovering living cells from cryopreserved cells includes thawing cryopreserved cells and diluting the thawed cell suspension with a diluent, wherein the dilution is performed in such a way that the maximum load of osmotic pressure at the time of dilution is equal to or less than 250 mOsm/second.

11 Claims, No Drawings

METHOD AND SYSTEM FOR RECOVERY
OF LIVING CELLS FROM
CRYOPRESERVED CELLS

CROSS-REFERENCES TO RELATED APPLICATIONS

This application is a continuation of International Application No. PCT/JP2015/057473 filed on Mar. 13, 2015, and which claims priority to Japanese Patent Application No. 2014-062311 filed on Mar. 25, 2014, the entire contents of both, which is incorporated herein by reference.

TECHNICAL FIELD

The present disclosure relates to a method and system for highly efficient recovery of living cells from cryopreserved cells by thawing.

BACKGROUND DISCUSSION

Efforts have been made in recent years toward the transplantation of various kinds of cells for the healing of damaged tissues. For example, attempts are being made to heal cardiac muscle tissues damaged by ischemic heart disease, such as angina pectoris and cardiac infarction, by means of transplantation with fetal cardiac muscle cells, skeletal muscle blast cells, and embryonic stem (ES) cells.

Such attempts have led to the development of cell structure formed by the use of scaffold and the development of sheet-like cell culture product in the form of sheet composed of cells (see JP-T-2007-528755, Japanese Patent Laid-open No. 2010-81829, and Japanese Patent Laid-open No. 2010-226991, for example).

The sheet-like cell culture product is expected to find use in the form of cultured epidermal sheet for damaged or scalded skin, in the form of corneal epithelium sheet for damaged cornea, and in the form of oral mucous membrane sheet for endoscopic resection of esophageal carcinoma.

Along with the recently established healing method which is based on the regenerative medicine, there are increasing instances for healing in recent years in which artificial tissue or sheet-like cell culture product in the form of three-dimensional structure is made from cryopreserved autologous cells, or in which autologous cells are recovered by thawing cryopreserved cells at the time of direct cell transplantation.

Cells can be preserved semipermanently by freezing in liquid nitrogen or the like. However, cells are subject to damage due to latent heat that occurs at the time of freezing and damage due to ice crystals which appear in the cells. Thus, it is impossible to entirely recover living cells from the cryopreserved cells. It is common practice to secure as many cells as necessary by culturing and proliferating cells obtained after the thawing of cryopreserved cells. Since the long term culturing is time-consuming, there has arisen a need for recovering as many living cells as possible without laborious steps. Common way to cope with this situation is by reducing physical damage to cells and increasing the number of living cells, which will be achieved by improving the methods for freezing and thawing.

The sheet-like cell culture product should preferably be prepared from autologous cells from the standpoint of limited rejection. The preparation of sheet-like cell culture product from autologous cells requires time for cell proliferation and differentiation, which limits the rate of preparation. In order to overcome this drawback, there has been proposed a method for preparing the sheet-like cell culture product. The method consists of seeding the cells at a specific density that permits the sheet-like cell culture product to be formed without substantial cell proliferation (see Japanese Patent Laid-open No. 2010-81829, for example). Due to the method, it has become possible to prepare a sheet-like cell culture product, which has a higher physical strength than before, in a shorter time than before.

The method for preparing the sheet-like cell culture product needs more cells than the conventional one. This makes it necessary to proliferate and culture beforehand the cells collected from the recipient and preserve the proliferated cells cryogenically for use. In the case where the sheet-like cell culture product is prepared by the method, however, the method does not give rise to any satisfactory sheet-like cell culture product, simply resulting in cell proliferation or cell differentiation, unless cells in a sufficient amount are seeded. The result is that the sheet-like cell culture product is not ready for transplantation if sufficient cells are not secured for the sheet-like cell culture product to be prepared immediately before transplantation. For this reason, it is common practice to recover as many living cells as possible by attempting to minimize physical and chemical damages to cells at the time of freezing and/or thawing cryopreserved cells.

SUMMARY

A method is disclosed for recovering living cells highly efficiently from cryopreserved cells and also provide a system for the method, and wherein the method and system can be achieved by reducing more than before physical and chemical damages to cryopreserved cells at the time of thawing for the recovery of living cells.

The freezing of cells is usually accomplished with the addition of a cryoprotectant so that cells are saved from physical damage due to ice crystals. A common example of the cryoprotectant is dimethylsulfoxide (DMSO). DMSO is known to exhibit cytotoxicity at approximately 37° C., which means that the cytotoxicity appears at the time of thawing the cryopreserved cells. Usually, for example, attempts are made to reduce cytotoxicity as much as possible by quick dilution.

In the course of study on the method for efficient recovery of living cells from cryopreserved cells, the present inventors found that the quicker the dilution of cell suspension after thawing for reduction of DMSO's cytotoxicity, the less the number of living cells recovered. This phenomenon is contrary to what has been observed before. As the result of their continued study on this phenomenon, the present inventors further found that the quick dilution greatly damages cells due to rapid change in osmotic pressure and that such damages to cells can be reduced by suppressing the load of osmotic pressure at the time of dilution, which leads to an increased survival ratio of cells. The result of these investigations led to the present disclosure.

A method is disclosed for recovering living cells from cryopreserved cells, including: thawing cryopreserved cells; and diluting the thawed cell suspension with a diluent, wherein the dilution is performed in such a way that the maximum load of osmotic pressure at the time of dilution is equal to or less than 250 mOsm/second.

In accordance with an exemplary embodiment, the diluent is added in such a way that the maximum load of osmotic pressure at the time of dilution is equal to or less than 50 mOsm/second.

In accordance with an exemplary embodiment, the diluent is added in such a way that the maximum load of osmotic pressure at the time of dilution ranges from 40 mOsm/second to 50 mOsm/second.

In accordance with an exemplary embodiment, the cells are skeletal muscle blast cells.

In accordance with an exemplary embodiment, the diluent contains the rinsing liquid resulting from rinsing of a container for cryopreservation from which the thawed cell suspension has been transferred to another container.

In accordance with an exemplary embodiment, a system is disclosed for thawing cryopreserved cells, including: (i) an actuating unit configured to inject a diluent; and (ii) an arithmetic control unit configured to determine the rate at which the actuating unit injects the diluent.

In accordance with an exemplary embodiment, the system further includes (iii) a measuring unit configured to measure osmotic pressure of liquid.

A kit is disclosed, which includes cells; and a culture substrate used for a method of producing a sheet-like cell culture product without necessity for proliferation culture, the method including a step of seeding at a density suitable to form the sheet-like cell culture product without substantial cell proliferation, wherein cells are those which have been recovered by any method disclosed herein.

DETAILED DESCRIPTION

The present disclosure is intended to reduce the number of cells dying from an abrupt change in osmotic pressure which has been neglected before, thereby increasing the number of recoverable living cells, by means of controlling the load of osmotic pressure. According to the present disclosure, cells which retain high viability even after freezing and thawing can be recovered. Therefore, the present disclosure permits to secure sufficient living cells without requiring the step of proliferation culture after thawing.

The present disclosure relates to a method for highly efficiently recovering living cells from cryopreserved cells and also to a system for the method.

The present disclosure will be described below in more detail with reference to the preferred embodiments thereof.

Method for Recovering Living Cells

One aspect of the present disclosure relates to a method for recovering living cells from cryopreserved cells, which includes steps of thawing cryopreserved cells and diluting with a diluent the suspension of thawed cells. This method is characterized in that the dilution is performed in such a way that the change in osmotic pressure due to dilution is kept sufficiently small.

The term "cryopreserved cells" used in the present disclosure usually means cryopreserved cells themselves. However, it occasionally means a unit of cryopreserved cells. In this case, the term "cryopreserved unit" means a group of cells, which are cryopreserved together in a tube, for example. Thus, the "cryopreserved cells" give upon thawing "a suspension of cells" which had been frozen.

The term "load of osmotic pressure at the time of dilution" as used in the present disclosure means the rate of change per unit time in the osmotic pressure which varies with addition of the diluent. The load of osmotic pressure varies depending on such factors as the rate of addition of the diluent (or the amount of diluent added per unit time) and the difference in osmotic pressure between the diluent and the liquid to be diluted (such as the suspension of thawed cells). The term "maximum load of osmotic pressure" as used in the present disclosure means the maximum value of the load of osmotic pressure, which varies as the diluent is added from the start of dilution to the completion of dilution.

The method according to the present disclosure is characterized in that the cell suspension obtained by thawing the cryopreserved cells is diluted in such a way that the change in osmotic pressure is kept sufficiently small during dilution. The recovery of living cells from cryopreserved cells by thawing is usually accomplished by adding a culture medium or the like to the suspension of thawed cells for dilution in order to lessen the influence of cytotoxic components existing in the suspension of thawed cells. The present inventors found that the dilution at an excessively high rate in the step of dilution causes a rapid change in the osmotic pressure of the suspension, with such a change damaging cells, thereby decreasing the survival ratio of living cells.

The dilution with a minimum change in osmotic pressure will reduce damages to cells, thereby increasing the yield of recovery of living cells. The method of reducing the change in osmotic pressure may be achieved by slowing the addition of the diluent or using a diluent, which only slightly varies in osmotic pressure from the cell suspension. These techniques are known to persons skilled in the art. What is preferable is to avoid using any diluent with cytotoxicity, thereby excluding any damages other than those caused by the load of osmotic pressure.

The diluent to be used in the present disclosure is not specifically restricted so long as it does not cause physical and chemical damages to cells. Examples of the diluent unrestrictedly include liquid culture medium, such as Dulbecco's modified Eagle's medium (DMEM), Hank's balanced salt solution, buffer solution, such as phosphate buffered saline (PBS), isotonic solution, such as physiological saline, and distilled water. They may optionally be incorporated with additional ingredients such as albumin.

In this specification, the unit "Osm" is used as the unit for osmotic pressure. "1 Osm" denotes an osmotic pressure equivalent to the osmotic pressure possessed by an ideal solution of 1 mol/L. The load of osmotic pressure at the time of dilution is expressed in terms of the rate of change in osmotic pressure per second at room temperature (unit: Osm/second). However, any other arbitrary unit may be selected so long as it can express the magnitude of the change in osmotic pressure. Such units may include the speed of addition of the diluent and the speed of increase in volume or weight.

The load of osmotic pressure may be obtained by measuring in real time the change in osmotic pressure or by calculating an average of change per unit time between two measurements made at two different points of time. In the case where a diluent is added at a constant rate, the maximum load of osmotic pressure during dilution may be obtained from the difference between two osmotic pressures measured at the start of addition and at a point of elapsed time (for example, one second in the above-mentioned example of the present disclosure) after the start of addition. This is based on an assumption that the load of osmotic pressure reaches the maximum value when the addition of diluent starts and then gradually decreases according as the addition of diluent increases.

The method employed in the embodiment will be described step by step in the following.

Thawing of Cryopreserved Cells

The step of thawing cryopreserved cells may be accomplished by under any conditions known in the technical field concerned. Usually, thawing should be performed by instantaneous warming with the help of a water bath or the like kept at approximately 37° C. This is because slow thawing tends to cause physical damages to cells due to ice crystals. It is also possible to use any other method than above which is employed in the technical field concerned in order to improve the recovery of living cells.

The method according to the present disclosure can be applied to any kind of cells known in the technical field concerned, which are capable of cryopreservation. Preferable examples of such cells include somatic stem cells, such as embryonic stem cells, nerve stem cells, hematopoietic stem cells, and mesenchymal stem cells, and blast cells, such as fibroblast cells, skeletal muscle blast cells, and osteoblast cells, which are used for regenerative medicine. In accordance with an exemplary embodiment, for example, more desirable among them are somatic stem cells and blast cells which can be sampled and proliferated as autologous cells. Skeletal muscle blast cells are most desirable from the standpoint of availability and handleability. In accordance with an exemplary embodiment, It can be desirable to use cells in the logarithmic growth phase from the standpoint of high recovery ratio of living cells.

The amount of cryopreserved cells may vary according to the capacity of the container used for cryopreservation. Each container should be generally given a suspension of cells for cryopreservation, which has a cell density adjusted to, for example, approximately $1 \times 10^5$ to $5 \times 10^7$ cells/ml. This value may be used as the parameter for the calculation of living cells to be recovered from the unfrozen cell suspension, in view of the fact that all the cryopreserved cells should ideally be recovered in the form of living cells.

The cryopreserving liquid is not specifically restricted so long as it is selected from those used for cryopreservation of cells in the technical field concerned which are sold from a lot of companies. Any ordinary cell culture medium may also be used, which is incorporated with a cryoprotectant, such as dimethylsulfoxide (DMSO) and glycerol, in an amount of approximately, for example, 1% to 20%, preferably approximately 5% to 10%. The culture medium may also be replaced by 100% serum.

The containers for cryopreserved cells may be selected from those which are commonly used in the technical field concerned. Their examples include commercial cryovials, ampoules, and cryopreserving bags.

Dilution of Cell Suspension

The cell suspension resulting from thawing is likely to contain a cytotoxic component (such as DMSO), as mentioned above. The effect of cytotoxicity can be alleviated by dilution. According to the method of the present disclosure, this dilution is performed in such a way as to slow the change in osmotic pressure, or to minimize the load of osmotic pressure, so that the thawed cells survive at a high ratio.

The term "sufficiently slow change in osmotic pressure" as used in the method of the present disclosure varies in its threshold value depending on the kind of cells and the condition and temperature of thawing. In accordance with an exemplary embodiment, the maximum load of osmotic pressure should be equal to or less than approximately, for example, 250 mOsm/second, preferably equal to or less than approximately 220 mOsm/second, more preferably equal to or less than approximately 100 mOsm/second, and most desirably equal to or less than approximately 50 mOsm/second, in an exemplary case where the cryopreserving liquid is an ordinary one (such as DMEM medium containing approximately 10% DMSO) and the diluent is an ordinary one (such as commercial DMEM medium).

The dilution should preferably be performed as rapidly as possible, because excessively slow dilution causes damage to cells due to the cryotoxic component in the cell suspension which can invoke other factors than the load of osmotic pressure. The method according to the present disclosure does not need a specific lower limit for the maximum load of osmotic pressure. However, it should preferably be equal to or greater than approximately, for example, 2 mOsm/second, more preferably equal to or greater than approximately 20 mOsm/second, and most desirably equal to or greater than approximately 40 mOsm/second, in the case where the method employs an ordinary cryopreserving liquid, such as DMEM medium containing approximately 10% DMSO, and an ordinary diluent, such as commercial DMEM medium.

According to one preferred embodiment of the present disclosure, the maximum load of osmotic pressure should be, for example, 2 mOsm/second to 250 mOsm/second, preferably 2 mOsm/second to 220 mOsm/second, more preferably 20 mOsm/second to 100 mOsm/second, and most desirably 40 mOsm/second to 50 mOsm/second, in view of the amount of recoverable living cells.

The dilution step may be carried out in such a way that the suspension of thawed cells is held in the container for cryopreservation or transferred to the other container. In the latter case, the container for cryopreservation to which the cell suspension has been transferred should be rinsed with a diluent and the resulting rinsing liquid should be added to the cell suspension. This procedure can be necessary to raise the survival ratio of thawed cells. Such addition of the rinsing liquid is equivalent to the dilution specified in the present disclosure. Thus, according to one embodiment of the present disclosure, the diluent can include the rinsing liquid resulting from rinsing the cryopreserving container from which the cell suspension has been transferred to the other container.

As mentioned above, the method according to the present disclosure has the maximum load of osmotic pressure affected most easily by the diluent to be added first to the suspension of thawed cells. Therefore, in one embodiment of the present disclosure, the maximum load of osmotic pressure is defined as that which is observed during the period in which the suspension is diluted thrice. In another embodiment of present disclosure, the maximum load of osmotic pressure is defined as that which is observed during the period in which the suspension is diluted twice.

According to one preferred embodiment of the present disclosure, the dilution should be performed in such a way that the maximum load of osmotic pressure is maintained in response to the osmotic pressure measured. The measurement of osmotic pressure may be performed continuously at all times or intermittently with certain intervals, for example, one second, 10 seconds, 30 seconds, or one minute. Any method known in the technical field concerned may be used for the measurement of osmotic pressure. Measurement with an osmometer is one example of such methods.

System for Thawing Cryopreserved Cells

One aspect of the present disclosure relates to a system to thaw cryopreserved cells and recover living cells highly efficiently. In accordance with an exemplary embodiment, the system can include (i) an actuating unit for injection of diluent and (ii) an arithmetic control unit to determine and control the rate at which the actuating unit injects the diluent.

The actuating unit for injection of the diluent may have any shape so long as it is capable of injection. A desirable shape can be one which permits the diluent to drip down. The actuating unit should be capable of adjusting the rate at which the diluent is added according to a signal from the arithmetic control unit.

The arithmetic control unit is intended to determine and control the rate at which the diluent is injected from the actuating unit. The injection rate may be established according to the previously entered value or calculated from the instantaneous osmotic pressure of the cell suspension. In the latter case, but it is not limited by the following, the initial amount of cell suspension and the osmotic pressure are entered and the existing osmotic pressure and addition rate can be determined, for example, from the amount of diluent added, osmotic pressure, and temperature. Alternatively, the change in the rate of addition of the diluent can also be previously programed.

In the case where the rate of addition of the diluent is calculated from the instantaneous osmotic pressure of the cell suspension, the system according to the present disclosure may further include a measuring unit to measure the osmotic pressure of the liquid. In this case, the arithmetic control unit will be able to determine the rate of addition according to the information entered from the measuring unit.

The system according to the present disclosure is intended to thaw cryopreserved cells and recover living cells from them. It may include any arbitrary unit to thaw cryopreserved cells in addition to the foregoing actuating unit, arithmetic control unit, and measuring unit. Such additional units would be apparent to those skilled in the art because the equipment to thaw cryopreserved cells and recover living cells from them are known in the technical field concerned. Examples of such additional units unrestrictedly include a thermostat unit, which keeps the system at a constant temperature during thawing cryopreserved cells, a pipetting unit which transfers the cell suspension from the cryopreserving container, a spinning unit which centrifuges the cell suspension, and a counter unit which counts the number of living cells.

Method for producing a sheet-like cell culture product and a kit designed therefor As mentioned above, those cells which have been recovered by the recovery method according to the present disclosure are adequate for use particularly in the case where they are used as such without any proliferation step. Thus, one aspect of the present disclosure relates to a method for producing a sheet-like cell culture product from cells recovered by the recovery method of the present disclosure.

The term "sheet-like cell culture product" as used in the present disclosure denotes a product composed of cells joined together in sheet form. The cells constituting this product may be joined together directly or indirectly with one another, with cellular elements such as adhesive molecules placed between them (in the former case) and/or an intermediate substance interposed between them (in the latter case). The intermediate substance is not specifically restricted so long as it is capable of physically (or mechanically) joining cells together. It can include, for example, extracellular matrices. In accordance with an exemplary embodiment, the intermediate substance should preferably be one which is derived from cells, particularly one which is derived from cells constituting the cell culture product. The cells should be joined together at least physically (or mechanically); they may also be joined together functionally, such as chemically and electrically. The sheet-like cell culture product may be of monolayer structure or multilayer (laminated) structure (with, for example, two, three, four, five, or six layers).

The sheet-like cell culture product should preferably be one which is free of scaffold (support). The scaffold (which is known in the technical field concerned) is used to keep the sheet-like cell culture product physically integral in such a way that cells are allowed to adhere to the surface or inside thereof. A known example of the scaffold is a film of polyvinylidene difluoride (PVDF). The sheet-like cell culture product according to the present disclosure may be one which remains physically integral without such scaffold. In addition, the sheet-like cell culture product should preferably be one which is composed merely of a substance derived from cells constituting the cell culture product and free from other substances.

The producing method according to the present disclosure can include a step of thawing cells which have been cryopreserved by the recovery method according to the present disclosure, and recovering thawed cells, and a step of seeding thus recovered cells, thereby forming the sheet-like cell culture product.

The producing method according to the present disclosure may further include a step of cleaning cells after the step of thawing and recovering cryopreserved cells and before the step of forming the sheet-like cell culture product. The washing of cells may be performed in any known way. Typically, with no restrictions, it is performed by suspending cells in a fluid, centrifuging the suspension, discarding the supernatant, and recovering precipitated cells. The solution for suspension is a culture solution (or culture medium) or physiological buffer solution (for example, PBS and Hank's balanced salt solution (HBSS)), which may or may not contain a cleaning liquid, such as serum or serum component (e.g., serum albumin). The step of cleaning cells may be performed by repeating suspension, centrifuging, and recovery once or several times (for example, two, three, four, five times, etc.). According to one embodiment of the present disclosure, the step of cleaning cells is performed immediately after the step of thawing frozen cells.

The producing method according to the present disclosure can include the step of forming the sheet-like cell culture product, which may be performed by any known technique. Some examples of such techniques are described in JP-T-2007-528755, Japanese Patent Laid-open No. 2010-81829, and Japanese Patent Laid-open No. 2010-226991. The step of forming the sheet-like cell culture product may be carried on a culture substrate. The step of forming the sheet-like cell culture product may include additional steps of seeding cells on the culture substrate and making the seeded cells into a sheet. In its one embodiment, the producing method according to the present disclosure does not include the step of proliferating cells between the step of thawing and recovering cells and the step of forming the sheet-like cell culture product.

The culture substrate is not specifically restricted so long as it permits cells to form thereon the cell culture product. It includes, for example, containers of various materials and a solid or semisolid surface in the container. The container is not specifically restricted so long as it is made of a structure and a material impervious to such liquid as culture solution. Examples of such a material include polyethylene, polypropylene, Teflon (registered trademark), polyethylene terephthalate, polymethyl methacrylate, nylon-6,6, polyvinyl alcohol, cellulose, silicone, poly-styrene, glass, polyacrylamide, polydimethyl acrylamide, and metal (such as iron, stainless steel, aluminum, copper, and brass). The container should preferably be one which has at least one flat surface. Examples of such a container, which are not specifically restricted, include cell culture dishes and cell culture bottles. The container may have a solid or semisolid surface therein. Examples of the solid surface include various kinds of plates and containers mentioned above. Examples of the semisolid surface include soft polymer matrices made of gel. The culture substrate may be prepared from the above-mentioned materials or acquired from commercial sources. Preferable culture substrate is not specifically restricted so long as it has an adhesive surface that permits the sheet-like cell culture product to be formed thereon. Examples can include a substrate with a hydrophilic surface, such as polystyrene with corona discharge treatment; a substrate which is surface-coated with a hydrophilic compound, such as collagen gel and hydrophilic polymer; a substrate which is surface-coated with an extracellular matrix, such as collagen, fibronectin, laminin, vitronectin, proteoglycan, and glycosaminoglycan, or a cell adhesion factor, such as cadherin family, selectin family, and integrin family. Such substrates are commercially available (for example, Corning® TC-Treated Culture Dish from Corning).

The substrate of the culture substrate may be one which has its surface coated with a various kind of material which imparts desired properties and characteristics. Known examples of the coating material include polymer, serum, growth factor, and steroid. They may be properly selected by those skilled in the art according to the desired properties and characteristics for the culture substrate. For example, if the substrate surface is required to change in hydrophilicity or hydrophobicity depending on temperature, the coating material should preferably be selected from the following: (meth)acrylamide compounds and N-alkyl-substituted (meth)-acrylamide derivatives (such as N-ethylacrylamide, N-n-propylacrylamide, N-n-propylmethacrylamide, N-isopropylacrylamide, N-isopropylmethacrylamide, N-cyclopropylacrylamide, N-cyclopropylmethacrylamide, N-ethoxyethylacrylamide, N-ethoxyethylmethacrylamide, N-tetrahydro-furfuryl acrylamide, and N-tetrahydro-furfuryl methacrylamide); N,N-dialkyl-substituted (meth)acrylamide derivatives (such as N,N-dimethyl(meth)acrylamide, N,N-ethylmethyl-acrylamide and N,N-diethylacrylamide); (meth)acrylamide derivatives having cyclic groups (such as 1-(1-oxo-2-propenyl)-pyrrolidine, 1-(1-oxo-2-propenyl)-piperidine, 4-(1-oxo-2-propenyl)-morpholine, 1-(1-oxo-2-methyl-2-propenyl)-pyrrolidine, 1-(1-oxo-2-methyl-2-propenyl)-piperidine, and 4-(1-oxo-2-methyl-2-propenyl)-morpholine); and temperature-responsive material composed of vinyl ether derivatives (such as homopolymer or copolymer of methyl vinyl ether). There are commercial products of culture dishes coated with a temperature-responsive material (such as UpCell® from CellSeed Inc.). They may be used for the producing method according to the present disclosure.

The culture substrate may be coated with serum so that it helps form a sheet-like cell culture product which is densely composed of cells. The term "serum coating" means that the culture substrate is in such a state that its surface bears serum components. This state is not restricted; it may be realized by treating with serum the culture substrate. The treatment with serum may be accomplished by keeping the culture substrate in contact with serum, followed by optional incubation for a prescribed period of time. The serum for coating may be that of the same or different species derived from the seeded cells. In accordance with an exemplary embodiment, the former is preferable. The most desirable serum is autologous serum obtained from individuals derived from seeded cells.

The seeding of cells onto the culture substrate may be accomplished by means of any known technique under any conditions. One way of seeding of cells onto the culture substrate is by injection of a cell suspension in which cells are suspending in a culture solution into the culture substrate (or culture container). Injection of cell suspension may be performed by using a dropper or pipette, which is suitable for injection of cell suspension.

According to a preferred embodiment of the present disclosure, seeding should be performed with an adequate cell density in such a way that seeded cells form a sheet-like cell culture product without substantial proliferation. The term "adequate cell density in such a way that seeded cells form a sheet-like cell culture product without substantial proliferation" means that the seeded cells form the sheet-like cell culture product when they are cultured in a non-proliferating culture solution which is substantially free of growth factor. For example, it is necessary for skeletal muscle blast cells to be seeded onto the culture substrate at a density of about 6,500 cells/cm$^2$ if the seeded cells are to form a sheet-like cell culture product by using a culture solution containing a growth factor (see JP-T-2007-528755, for example). The cells seeded at such a cell density do not form any sheet-like cell culture product as desired even though they are cultured in a culture solution free of growth factor. The cell density for seeding in the embodiment of the present disclosure is higher than that which is used for the culture solution containing growth factor. Specifically, such a cell density is typically equal to or greater than approximately $1.0 \times 10^5$ cells/cm$^2$ for skeletal muscle blast cells. The upper limit of the cell density for seeding is less than, for example, approximately $3.4 \times 10^6$ cells/cm$^2$ for skeletal muscle blast cells. It is not specifically restricted so long as the seeded cells form the sheet-like cell culture product smoothly without differentiation.

The step of making the seeded cells into a sheet may also be accomplished by any known technique under any conditions. Some of such known techniques are found in JP-T-2007-528755, Japanese Patent Laid-open No. 2010-81829, and Japanese Patent Laid-open No. 2010-226991, for example. Presumably, conversion of cells into a sheet takes places adhesion between cells through adhesive molecules or extracellular matrices which function as the cell-to-cell adhesion mechanism. Consequently, the step of making the seeded cells into a sheet can be achieved by culturing cells under the condition which permits cells to adhere to one another.

The producing method according to the present disclosure may employ any culture solution, which is not specifically restricted so long as it keeps cells alive. Examples of the culture solution can include amino acids, vitamins, and those which are composed mainly of electrolytes. According to one embodiment of the present disclosure, the culture solution is one which is based on the minimal essential medium for cell culture. Examples of culture solution can include DMEM, minimum essential medium (MEM), F12, DMEM/F12, DME, Roswell park memorial institute (RPMI) 1640, molecular, cellular and developmental biology (MCDB) (MCDB102, 104, 107, 120, 131, 153, and 199), Leibovitz 15 (L15), skeletal muscle cell basal medium (SkBM), and RITC80-7. Most of them are commercially available and their compositions are known. When they are employed for the producing method of the present disclosure, their composition may be properly altered according to the species and conditions of cells.

In one embodiment of the producing method according to the present disclosure, the step of freezing cells may be followed by the step of forming the sheet-like cell culture product without substantial cell proliferation. This procedure helps further increase the activity of the sheet-like cell culture product.

The term "without substantial cell proliferation" means a situation in which cells do not proliferate beyond the limit of measurement errors. The cell proliferation may be evaluated from difference between the number of cells counted at the time of seeding and the number of cells counted after the sheet-like cell culture product has been formed. According to the present disclosure, the number of cells counted after the formation of the sheet-like cell culture product should be, for example, equal to or less than approximately 300% of the cell counted at the time of seeding, preferably equal to or less than approximately 200%, more preferably equal to or less than approximately 150%, much more preferably equal to or less than approximately 125%, and most desirably equal to or less than about 100%.

Since the proliferation of cells depends on various conditions, such as the number of cells seeded (or the density of cells seeded), the environment of culture (or the culture period and culture temperature), and the composition of the culture medium, it is possible to substantially prevent the proliferation of cells by controlling the above-mentioned conditions. If the density of cells seeded is increased, the sheet-like cell culture product within a comparatively short period of time can be obtained while preventing the proliferation of cells. Consequently, according to the present disclosure, it can be desirable to control the proliferation of cells by adjusting the density of cells seeded among the above-mentioned conditions. The foregoing has described the density of cells which permits the sheet-like cell culture product to be formed without substantial proliferation of cells. Therefore, according to one preferred embodiment, the step of thawing cells is followed by the step of making the thawed cells into a sheet, with the step of cell proliferation skipped, under the condition which substantially prevents the cell proliferation.

Another aspect of the present disclosure relates to a kit used to produce the above-mentioned sheet-like cell culture product. The kit partly or entirely includes the components for production of the sheet-like cell culture product which does not experience the step of cell proliferation.

The kit according to the present disclosure is not specifically restricted; it may be composed of cells which form the sheet-like cell culture product, culture solution, culture dish, instruments, and instructions for the method of producing the sheet-like cell culture product. The cells may be cryopreserved cells or cells recovered by the recovery method according to the present disclosure. The instruments include pipette, dropper, tweezers, etc. The instructions include user's manual and any medium which contains information about the method for production and the method for recovery of cryopreserved cells defined in the present disclosure. The medium includes flexible disk, compact disc (CD), digital versatile disc (DVD), Blu-ray disc, memory card, universal serial bus (USB) memory, etc.

The present disclosure will be described in more detail with reference to the embodiments thereof, with no intention to limit the scope thereof.

EXAMPLES

Example 1

Interrelation Between the Rate of Addition of Diluent and the Survival Ratio of Cells The following procedure was carried out to thaw cryopreserved cells and recover living cells. First, a cryotube (1.8 mL) containing skeletal muscle blast cells, which had been cryopreserved therein, was placed in a water bath kept at 37° C. for three to four minutes, so that the cryopreserved cells were thawed. The resulting suspension of the thawed cells was transferred from the cryotube to a conical tube (225 mL). The cryotube was rinsed with a cleaning liquid (1 mL) composed of HBSS and albumin, for recovery of cells remaining in the cryotube. The resulting rinsing liquid was added to the cell suspension at a different rate of addition. The cleaning liquid (30 mL) was added to the conical tube at a different rate of addition in the same way as the above-mentioned rinsing liquid. The content of the conical tube was centrifuged at 4° C. for seven minutes with a centrifugal force of 240 g, and the supernatant was discarded. The cleaning liquid (30 mL) was added again, followed by centrifugation at 4° C. for seven minutes with a centrifugal force of 240 g, and the supernatant was discarded. The cleaning liquid (5 mL) was added to give the cell suspension as desired.

A portion of the thus obtained cell suspension was extracted and mixed with trypan blue. The number of cells were counted. The result of the cell count was used to calculate the number of living cells remaining after thawing. The survival ratio of living cells was calculated according to the following formula.

Cell survival ratio (%)=Number of living cells remaining after thawing/Number of total cells counted after thawing×100

The rinsing liquid was added at a rate equal to or greater than 1.2 mL/minute, 4.0 mL/minute, 15.0 mL/minute, and 360 mL/minute. The cleaning liquid was added at a rate four times as large as that of the rinsing liquid in the case where it was added dropwise. The cleaning liquid was added at a rate twice as large as that of the rinsing liquid in the case where it was added non-dropwise.

The maximum load of osmotic pressure was calculated according to the following formula. Incidentally, the initial osmotic pressure of the cell suspension was assumed to be 1400 mOsm, and the osmotic pressure of the diluent was assumed to be 300 mOsm.

Maximum load of osmotic pressure (mOsm/second)= [1400 mOsm−(1400 mOsm×liquid amount (mL)+300 mOsm×rate of addition (mL/second)×1 second)/(liquid amount (mL)+rate of addition (mL/second)×1 second)]/1 second      Formula 1

The results are shown in the table below. Incidentally, in the table, the amount at the time of start of dilution indicates the amount of cell suspension at the time of start of dilution.

TABLE 1

| Condition | Amount at start of dilution (mL) | Diluent | Rate of addition (mL/minute) | Maximum load of osmotic pressure (mOsm/second) | Cell survival ratio (%) |
|---|---|---|---|---|---|
| Dropping 1 | 1.0 | Rinsing liquid | 0.2 | ca. 4 | 91.0 ± 3.6 |
|  |  | Cleaning liquid | 0.8 |  |  |

TABLE 1-continued

| Condition | Amount at start of dilution (mL) | Diluent | Rate of addition (mL/minute) | Maximum load of osmotic pressure (mOsm/second) | Cell survival ratio (%) |
|---|---|---|---|---|---|
| Dropping 2 | 1.0 | Rinsing liquid | 0.67 | ca. 12 | 90.9 ± 2.2 |
| | | Cleaning liquid | 2.67 | | |
| Dropping 3 | 1.0 | Rinsing liquid | 2.5 | ca. 44 | 91.5 ± 1.4 |
| | | Cleaning liquid | 10.0 | | |
| Dropping 4 | 1.0 | Rinsing liquid | 15.0 | ca. 220 | 90.0 ± 2.3 |
| | | Cleaning liquid | 60.0 | | |
| Dropping 5 | 0.2 | Rinsing liquid | 15.0 | ca. 610 | 83.0 ± 1.0 |
| No-Dropping | 1.0 | Rinsing liquid | 60 or more | ca. 550 | 87.1 ± 0.9 |
| | | Cleaning liquid | 120 or more | | |

In the case of dropping patterns 1 to 4, the ratio of cell survival was greater than 90% on average. By contrast, it was approximately 87% in the case of no-dropping. In the case where dropping is combined with dilution, the maximum load of osmotic pressure was approximately 610 mOsm/second under the condition (Dropping 5) in which the amount of cell suspension was decreased. In this case, the ratio of cell survival was approximately 83% on average. The highest ratio of cell survival was obtained in the case of Dropping 3 where the maximum load of osmotic pressure was approximately 44 mOsm/second among Droppings.

The detailed description above describes a method for highly efficiently recovering living cells from cryopreserved cells by thawing, and also to a system for the method puncture member. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A method for recovering living cells from cryopreserved cells, comprising:

thawing cryopreserved cells;

diluting a suspension of the thawed cryopreserved cells by dripping two different diluents into a container containing the suspension of the thawed cryopreserved cells, the dripping of the two different diluents into the container containing the suspension of the thawed cryopreserved cells including starting the dripping of a first one of the two different diluents into the container to begin the diluting and then stopping the dripping of the first diluent into the container containing the suspension of the thawed cryopreserved cells to complete the dilution with the first diluent, the dripping of the first diluent into the container from the starting of the dripping to the stopping of the dripping being performed at a constant rate of 2.5 mL/minute to 15.0 mL/minute throughout;

the dripping of the two different diluents into the container containing the suspension of the thawed cryopreserved cells including starting dripping a second one of the two different diluents into the container to begin the diluting and then stopping the dripping of the second diluent into the container to complete the dilution with the second diluent, the dripping of the second diluent into the container from the starting of the dripping to the stopping of the dripping being performed at a constant rate of 10 mL/minute to 60 mL/minute throughout; and performing the dilution such that a maximum load of osmotic pressure throughout the diluting is 44 mOsm/second to 220 mOsm/second and the cell survival ratio is greater than 90%.

2. The method according to claim 1, comprising:
performing the dilution such that the maximum load of osmotic pressure at the time of dilution ranges from 44 mOsm/second to 100 mOsm/second.

3. The method according to claim 1, wherein the cells are skeletal muscle blast cells.

4. The method according to claim 1, wherein the first diluent contains rinsing liquid resulting from rinsing of a container for cryopreservation from which the thawed cell suspension has been transferred to another container.

5. The method according to claim 1, wherein the thawing of cryopreserved cells comprises:
thawing the cryopreserved cells at approximately 37° C.; and
wherein the cryopreserved cells have a cell density of $1 \times 10^5$ to $5 \times 10^7$ cells/ml.

6. The method according to claim 1, wherein the cells are somatic stem cells, embryonic stem cells, nerve stem cells, hematopoietic stem cells, mesenchymal stem cells, fibroblast cells, skeletal muscle blast cells, or osteoblast cells.

7. The method according to claim 1, wherein the first and/or second diluent comprises
Dulbecco's modified Eagle's medium (DMEM).

8. The method according to claim 1, wherein the first diluent is a rinsing liquid and the second diluent is a cleaning liquid, the rinsing liquid resulting from rinsing a container for cryopreservation from which the thawed cell suspension has been transferred to the container containing the suspension of the thawed cryopreserved cells, the dripping of the rinsing liquid occuring before the dripping of the cleaning liquid into the container containing the suspension of the thawed cryopreserved cells.

9. A method for recovering living cells from cryopreserved cells, comprising:

thawing cryopreserved cells;

diluting a suspension of the thawed cryopreserved cells by first introducing a first diluent into a container containing the suspension of the thawed cryopreserved cells followed by introducing a second diluent into the container containing the suspension of the thawed cryopreserved cells, the first diluent having a composition different from the composition of the second diluent, the introducing of the first diluent into the container containing the suspension of the thawed cryopreserved cells including starting introduction of the first diluent into the container to begin the dilution with the first diluent and then stopping the introduction of the first diluent into the container to complete the dilution with the first diluent, the introduction of the first diluent into the container from the starting of the introduction of the first diluent to the stopping of the introduction of the first diluent being performed at a constant rate of 2.5 mL/minute to 15.0 mL/minute throughout, the introducing of the second diluent into the container containing the suspension of the thawed cryopreserved cells including starting introduction of the second diluent into the container to begin the dilution with the second diluent and then stopping the introduction of the second diluent into the container to complete the dilution with the second diluent, the introduction of the second diluent into the container from the starting of the introduction of the second diluent to the stopping of the introduction of the second diluent being performed at a constant rate of 10 mL/minute to 60 m L/minute throughout, the first and second diluents being one or more of the following:

Dulbecco's modified Eagle's medium (DMEM), a buffer solution, phosphate buffered saline (PBS), an isotonic solution, or distilled water; and performing the dilution such that a maximum load of osmotic pressure at the time of dilution is 44 mOsm/second to 220 mOsm/second and the cell survival ratio is greater than 90%.

10. The method according to claim 9, further comprising: adding albumin to the first diluent and/or the second diluent.

11. The method according to claim 9, wherein the constant rate at which the first diluent is introduced into the container differs from the constant rate at which the second diluent is introduced into the container.

* * * * *